United States Patent [19]
Acosta et al.

[11] Patent Number: 5,922,766
[45] Date of Patent: Jul. 13, 1999

[54] PALATABLE ELEMENTAL MEDICAL FOOD

[76] Inventors: Phyllis J. B. Acosta, 1287 Gemstone Sq. West, Westerville, Ohio 43081; Marlene W. Borschel, 340 E. North St., Worthington, Ohio 43085; Patricia A. Reynolds, 5700 Jousting La., Columbus, Ohio 43231; Christopher T. Cordle, 92 S. Preston St., Centerburg, Ohio 43011-0016; Geralyn O. Duska-McEwen, 336 Spruce Hill Dr., Gahanna, Ohio 43230

[21] Appl. No.: 08/887,001

[22] Filed: Jul. 2, 1997

Related U.S. Application Data

[51] Int. Cl.$^6$ .................................................. A61K 31/415
[52] U.S. Cl. ..................... 514/561; 514/400; 514/419; 514/423; 514/556; 514/562; 514/565; 514/566; 514/578; 426/72; 426/601; 426/658; 426/801
[58] Field of Search .............................. 426/72, 801, 601, 426/658; 424/440; 514/400, 419, 423, 556, 561, 562, 565, 566, 578

[56] References Cited

U.S. PATENT DOCUMENTS

| | | |
|---|---|---|
| Re. 35,233 | 5/1996 | Smith et al. . |
| 4,414,238 | 11/1983 | Schmidl . |
| 4,670,268 | 6/1987 | Mahmoud ................................. 426/72 |
| 5,234,702 | 8/1993 | Katz et al. . |
| 5,326,569 | 7/1994 | Acosta et al. ........................... 424/440 |
| 5,340,603 | 8/1994 | Neylan et al. . |
| 5,411,751 | 5/1995 | Grissinger et al. . |
| 5,411,757 | 5/1995 | Buist et al. . |
| 5,438,042 | 8/1995 | Schmidl et al. . |
| 5,492,899 | 2/1996 | Masor et al. ............................. 514/47 |
| 5,550,146 | 8/1996 | Acosta et al. . |

FOREIGN PATENT DOCUMENTS

| | | |
|---|---|---|
| 0 560 989 | 9/1993 | European Pat. Off. . |
| 0 705 542 | 4/1996 | European Pat. Off. . |

OTHER PUBLICATIONS

Lifschitz, C.H. and Carrazza, F., Effect of formula carbohydrate concentration on tolerance and macronutrient absorption in infants with severe, chronic diarrhea, *The Journal of Pediatrics*, Sep. 1990, pp. 378–383.

Jirapinyo, P., Young, C., Srimaruta, N., Rossi, T., Cardano, A. Lebenthal, E., High–Fat Semielemental Diet in the Treatment of Protracted Diarrhea of Infancy, *Pediatrics*, vol. 86, No. 6, Dec., 1990, pp. 902–908.

Recommended Dietary Allowances, Subcommittee on the Tenth Edition of the RDAs, Food and Nutrition Board, Commission of Life Sciences, National Research Council, pp. 33, 57 and table 1989.

Vivonex® Pediatric Product Information, Sandoz Nutrition Corporation, Jun. 1994.

Neonate® One+ Product Information, SHS North America 1989.

Vivonex® Pediatric Handout, Sandoz Nutrition Corporation, 1994.

*Primary Examiner*—Rebecca Cook
*Attorney, Agent, or Firm*—J. Michael Dixon; Thomas D. Brainard

[57] ABSTRACT

This invention relates to a palatable elemental nutritional formula that is nutritionally complete for humans with specialized dietary needs. The nutritional of the present invention uses specific free amino acids to provide the source of amino nitrogen (protein equivalents) and a special blend of fats that provides 38 to 50% of the total Calories in a pleasant tasting formula. The nutritionally complete formula of this invention is useful for children having multiple protein allergies, short gut syndrome, sick gut, diarrhea and the like. More specifically, the nutritional product, in accordance with this invention, utilizes L-asparagine monohydrochloride and L-glutamine in place of L-aspartic acid and L-glutamic acid, respectively. In addition, the source of fat comprises soy, fractionated coconut oil (medium chain triglycerides), high oleic safflower oil and esterified glycerol emulsifiers. The level of fat Calories is about 38 to 50% of total Calories, which produces a product having a low osmolarity and provides required energy requirements in a small volume.

15 Claims, No Drawings

PALATABLE ELEMENTAL MEDICAL FOOD

FIELD OF THE INVENTION

This invention relates to improved enteral nutritional hypoallergenic formulas and more particularly to hypoallergenic formulas which taste good. In addition, the nutritional product of this invention provides a nutritionally complete hypoallergenic food for individuals with multiple food allergies, short gut syndrome, cystic fibrosis, pancreatic disease, gastroenteritis, inflammatory bowel disease, intractable diarrhea, malnutrition, protein maldigestion, infectious diseases or for patients with hypermetabolism, such as burn and trauma victims or cancer patients.

BACKGROUND OF THE INVENTION

Hypoallergenic formulas or compositions which are also referred to as elemental formulas, are characterized in that they contain immunologically unreactive protein hydrolysates or free amino acids. The protein hydrolysates comprise short peptide fragments and/or free amino acids instead of the intact protein found, for example, in cow's milk and soy protein based formulas. These short peptide fragments and free amino acids have been found to be less immunogenic or allergenic than intact proteins.

In addition to the protein hydrolysates and/or free amino acids, most nutritionally balanced elemental or hypoallergenic formulas contain carbohydrates, lipids, vitamins and minerals to provide a nutritionally complete formula. These formulas are utilized for feeding infants, children and adults who have allergies or sensitivities to intact protein and are often medically used in the treatment of cystic fibrosis, chronic diarrhea, small bowel resection, steatorrhea and protein-calorie malnutrition.

One well known problem in the preparation of elemental or hypoallergenic formulas is product instability. Extensive hydrolysis of the protein by acids, or enzymes is necessary to provide the short peptides and amino acids utilized in the formulas to render such formulas hypoallergenic. These extensively digested proteins or free amino acids have undesirable characteristics such as bad taste and loss of capacity to emulsify fat and thereby fail to form physically stable emulsions that do not evidence phase separation.

U.S. Pat. No. 4,414,238 to Schmidl et al. discloses an elemental diet composition comprising carbohydrates, amino acids and/or low molecular weight peptides and lipids. The elemental diet of this patent has a lipid component in the form of an emulsion consisting of lipids, an emulsifier selected from the group consisting of mono- and di-glycerides, and a starch modified with succinic anhydride.

U.S. Pat. No. 4,670,268 to Mahmoud discloses an enteral nutritional hypoallergenic formula which uses a starch modified by octenyl succinic anhydride, which is utilized as the sole lipid emulsifier, to provide a nutritionally well-balanced dietary formula that possesses excellent physical stability.

U.S. Pat. No. 5,411,751 to Crissinger discloses infant formulas which contain no more than subirritant levels of free, long-chain ($C_{16}$–$C_{22}$) fatty acids and triglycerides thereof. This patent teaches that digestion products of triglycerides, in particular, long-chain fatty acids and monoglycerides, can damage the intestinal epithelium of infants and thus could mediate the onset of disorders such as necrotizing enterocolitis. This patent does not suggest or disclose a palatable elemental or hypoallergenic medical food that is essentially free of L-glutamic acid and L-aspartic acid.

U.S. Pat. No. 5,234,702 to Katz et al. discloses a powdered nutritional product that uses an antioxidant system to protect the oil component comprising ascorbyl palmitate, beta carotene and/or mixed tocopherols and citrate. The teachings of this patent are incorporated herein by reference.

U.S. Pat. No. Re. 35,233, discloses a method of treating atrophy of skeletal muscle and intestinal mucosa which comprises enterally administering glutamine or a functional derivative thereof in the range of 0.4 to 3.0 g/kg/day.

The nutritional formula according to this invention has been carefully formulated to provide a nutritional product that can be the sole source of nutrition for patients consuming it. To provide effective nutrition to human infants, children and adults, the present invention, in its most specific embodiments, carefully considers the bioavailability of trace and ultratrace minerals and the dietary interactions involving trace elements. Thus, the teachings of Forbes et al, *Bioavailability of Trace Mineral Elements*, Ann. Rev. Nutr. 1983, 3:213–231 and Mills, *Dietary Interactions Involving the Trace Elements*, Ann. Rev. Nutr. 1985, 5:173–193, are incorporated herein by reference.

U.S. Pat. Nos. 5,326,569 and 5,550,146 to Acosta et al. disclose a generic powder base, rich in fats, carbohydrates., vitamins, minerals and trace elements which are admixed with specific amino acids to yield several different therapeutic products which are used in the nutritional support of adults and children having various inherited metabolic diseases. These patents do not suggest or disclose the nutritionally complete hypoallergenic formulas of this invention which are essentially free of L-glutamic acid and L-aspartic acid.

The etiology of a number of gastrointestinal conditions has been demonstrated to be caused in some cases by food protein allergens. One such gastrointestinal condition is eosinophilic gastroenteritis. Eosinophilic gastroenteritis is characterized by peripheral eosinophilia, eosinophilic infiltration of the bowel wall, and various gastrointestinal symptoms. In pediatric cases, food antigens are the most common cause of eosinophilic gastroenteritis. Administration of an elemental, hypoallergenic diet may be required for rapid recovery as even extensively hydrolyzed casein-based formulas such as Alimentum® Protein Hydrolysate Formula With Iron (Ross Products Division, Abbott Laboratories, Columbus, Ohio) contains peptide fragments large enough to evoke an allergic reaction in the most sensitive of allergic individuals.

U.S. Pat. No. 5,492,899 to Masor et al. discloses an enteral nutritional formula containing ribonucleotides at specified levels. The formula of this patent comprises carbohydrates, lipids, proteins, vitamins and minerals and four (4) specified nucleotides at specific levels and ratios. One preferred embodiment of the present invention includes the presence of nucleotides in the elemental hypoallergenic medical food. The teachings of U.S. Pat. No. 5,492,899 are incorporated herein by reference.

U.S. Pat. No. 5,340,603 to Neylan et al. relates to a hypercaloric formula which provides nutritional support for human infants having chronic lung disease. The formula of this patent has a Caloric density of at least 800 kcal per liter of formula and wherein not less than 56% of the total Calories in said formula is derived from fat. In addition, the hypercaloric formula of this reference contains not more than 15% of total Calories derived from a high quality protein source and from about 20 to 27% of total Calories from a carbohydrate source. The formula of this patent also includes m-inositol at a concentration of at least 50 mg per liter of formula.

U.S. Pat. No. 5,411,757 to Buist et al. relates to a balanced, palatable medical diet for treatment of patients with inborn errors of essential amino acid metabolism. The diet of this patent uses L-amino acids at specified weights and ratios. More specifically, this patent discloses a palatable medical diet wherein the protein equivalent of L-amino acids is formed by the acetylation or the esterification of the L-amino acids. In contrast, the present invention uses L-amino acids to supply the amino nitrogen (protein equivalent) except for the replacement of L-asparagine for aspartic acid and L-glutamine for glutamic acid.

A presently available product known as Vivonex® Pediatric is marketed by the Clinical Products Division of Sandoz Nutrition, Minneapolis, Minn. for the gastrointestinally impaired child. The Vivonex® Pediatric contains 100% free amino acids and has an osmolality at standard dilution of 1 kcal/ml of 490 mOsm/kg $H_2O$. This product derives 25% of total Calories from fat with 68% of those Calories from medium chain triglycerides.

Neocate® One+ marketed by Scientific Hospital Supplies, Inc. (SHS) North America, Gaithersburg, Md., is a pediatric elemental nutritional that is marketed in liquid and powdered forms and is designed for children over one year of age. This liquid product contains 100% of its amino nitrogen in the form of free L-amino acids and has an osmolality at standard dilution (100 kcal/100 ml) of 835 mOsm/kg $H_2O$. Neocate® One+ powder (unflavored), when mixed to yield 100 kcal/100 mL, has an osmolality of 610 mOsm/kg $H_2O$. These products contain 3.5 grams of fat per 100 mL at a Caloric density of 100 kcal/100 mL. Neocate®, also marketed by SHS in the U.K., Scandanavia and the USA, uses maltodextrin as the carbohydrate source, contains 11.4% of Calories from free L-amino acids and 44.3% of Calories from fat wherein the fat is a mixture of refined lard, peanut oil and coconut oil.

In general, the prior art elemental or hypoallergenic formulas suffer from poor taste (organoleptic properties), high osmolarity and low Caloric density. In contrast, the present invention has acceptable organoleptic properties thereby facilitating oral consumption by the patient which also increases patient compliance with diet restrictions. The improved organoleptic properties are accomplished in part, by essentially excluding L-glutamic acid and L-aspartic acid from the formula and replacing them with L-glutamine and L-asparagine monohydrate. Further, the present invention is differentiated from the prior art in that it contains a higher Caloric content from fat which assists in improving organoleptic properties; reduces osmolality and increases overall Caloric density. Further, the specific fat blend of the invention provides a balance of the essential fatty acids linoleic and α-linolenic, in a readily absorbable form.

SUMMARY OF THE INVENTION

The present invention relates to an improved elemental formula comprising carbohydrates, lipids, free L-amino acids, vitamins and minerals. The invention is based, in part, on the discovery that the use of medium chain triglycerides (MCT's) or fractionated coconut oil, soy oil, esterified glycerol emulsifiers and high oleic safflower oil as the lipid component, in combination with the use of L-asparagine monohydrate in place of L-aspartic acid and L-glutamine in place of L-glutamic acid, vastly improves the organoleptic properties of the hypoallergenic formula. The present invention also uses a high level of fat to result in a product having a low osmolarity and also provides needed energy requirements in a small volume.

One aspect of the present invention relates to the preparation of an elemental medical food that is essentially free of L-glutamic acid and L-aspartic acid. In the present invention, L-glutamic acid ($C_5H_9NO_4$, mol. wt. 147.13) is replaced with L-glutamine ($C_5H_{10}N_2O_3$, mol. wt. 146.15), the monoamide of glutamic acid and L-aspartic acid ($C_4H_7NO_4$, mol. wt. 133.10) is replaced with L-asparagine monohydrate ($C_4H_8N_2O_3 \cdot H_2O$, mol. wt. 150.13), the monoamide of aspartic acid with one molecule of water. As used herein and in the claims, the phrase "to be essentially free of L-glutamic acid and L-aspartic acid" means less than 5 mgs of each acid should be present in 100 gms of powdered product (less than 50 ppm).

The present invention also relates to a complete pediatric hypoallergenic formula suitable for feeding to children on allergen-free diets. The formula according to this invention uses free L-amino acids as the source of amino nitrogen and meets the recommended dietary allowances (RDA) for the 1 to 3 year old child in 1000 kcal and for the 4 to 6 year old child in 1500 kcal. As used herein and in the claims, the term "protein equivalent" means the amount of amino nitrogen in grams present in the formulation multiplied by 6.25.

There is disclosed an elemental medical food for administration to a human comprising a) a carbohydrate component which comprises from 38–56% of the total Caloric content of said food; b) a lipid component which comprises from 38–50% of the total Caloric content of said food and wherein said lipid component is a blend of high-oleic safflower oil, fractionated coconut oil (medium chain triglycerides), soy oil and esterified glycerols; and c) an amino acid component which comprises from 10–20% of the total Caloric content of said food and wherein the amino acid component is essentially free (less than 5 mgs per 100 gms of powdered product) of L-glutamic acid and L-aspartic acid. The term "essentially free" means each of the amino acids are at concentrations of less than 5 mgs per 100 gms (50 ppm) of powdered product.

There is also disclosed a method for providing nutrition support to a human suffering from a malady selected from the group consisting of multiple food allergies, short gut syndrome, cystic fibrosis, pancreatic disease, gastroenteritis, inflammatory bowel disease, intractable diarrhea, malnutrition, protein maldigestion, infectious diseases such as HIV, hypermetabolism, trauma, eosinophilic gastroenteritis and gastroesophogeal reflux; said method comprises administering to said human a hypoallergenic formula in accordance with the present invention.

More specifically, this invention relates to an elemental medical food and method of its use wherein the carbohydrate component comprises from 38 to 56% of the total Caloric content of the composition and wherein the lipid component comprises from 38 to 50% of the total Caloric content of the composition and wherein the amino acid or protein equivalent component comprises from 10 to 20% of the total Caloric content of the composition. In a more preferred embodiment, the lipid component comprises 38–46% of the total Caloric content of the composition. The lipid component of this invention supplies 2–8% by wt. of the powdered product as linoleic acid (5–15% of Calories) and 0.4 to 1.0% by wt. of the powdered product as α-linolenic acid (0.8–2% of total Calories).

Preferably, the carbohydrate component of this invention consists essentially of corn syrup solids at a dextrose equivalent (DE) of 23 or less.

A stabilizer system is used in the formula of this invention and can be a single component or a mixture of known stabilizers. As mentioned previously, a major challenge in developing an elemental nutritional is physical stability. Physical stability relates to the oil and water emulsion of the formula. Those skilled in the art understand that free amino acids and hydrolyzed proteins do not produce emulsions that are stable over time. It is important that the elemental medical foods of this invention possess acceptable physical stability as separation of the emulsion into water and oil phases greatly decreases the palatability of the formula and may result in inadequate nutrition.

The inventors herein have evaluated numerous emulsion stabilizers and have determined that esterified glycerol emulsifiers such as diacetyl tartaric esters of monoglycerides are very useful in the present invention. Diacetyl tartaric acid esters of monoglycerides (hereinafter "DATEM") are commercially available and generally regarded as safe for human consumption by the USFDA. Representative DATEM emulsion stabilizers useful in the present invention include the Panodan® line of emulsion stabilizers sold by Grinsted Products, Inc. of Kansas, U.S.A. Panodan® is made from edible refined vegetable fat.

In one embodiment of the present invention, the DATEM emulsion stabilizer is the sole emulsion stabilizer and is present in the elemental medical food of this invention at a level of up to 8% by weight of the lipid. DATEM is grouped in the lipid component since upon ingestion, esterases cleave the fatty acid moiety from the tartaric acid moiety. The fatty acid then is absorbed and metabolized while the tartaric acid clears the body un-metabolized. The profile of Panodan® emulsion stabilizer sold by Grinsted is as follows:

| Component | Wt % |
| --- | --- |
| Fatty Acid | |
| 14:0 | 0.1 |
| 16:0 | 6.6 |
| 18:0 | 54.5 |
| 18:1 | 0.3 |
| 20:0 | 0.4 |
| Diacetyl tartaric Acid | 38.1 |

Another important aspect of the present invention relates to the use of an antioxidant system to lessen oxidation of the lipid component. Those skilled in this art will appreciate that the use of unsaturated oils in a powdered elemental product present special problems. To overcome the oxidation (spoilage) of the oils in the powdered product, the present invention, in one preferred embodiment, uses an antioxidant system comprising ascorbyl palmitate, beta carotene and citrate. The teachings of U.S. Pat. No. 5,234,702 to Katz et al., entitled ANTIOXIDANT SYSTEM FOR POWDERED NUTRITIONAL PRODUCTS, are incorporated herein by reference.

DETAILED DESCRIPTION OF THE INVENTION

All of the components of the inventive formulation are commercially available from numerous sources. For example, the carbohydrate source which is preferably corn syrup solids with a DE of less than 23 is available from Grain Processing Corporation, Muscatine, IA. The amino acids are available from Kyowa Hakko, Ajinomoto and Tanabe of Japan, and Degussa of Germany. The lipids are available from Stepan Co., Maywood, N.J. and California Oils, Richmond, Calif. The L-glutamine component is available from Kyowa Hakko of Japan and the L-asparagine monohydrate is available from Degussa.

In accordance with this invention, the osmolality of the formula can range from 300 to 400 mOsm/kg $H_2O$, and more preferably from 350 to 375 mOsm/kg $H_2O$ when 4.2 g of said powdered composition is added to water to yield 29.57 ml of formula. As one skilled in this art will appreciate, the osmolality of the formula will vary with the concentration or Caloric density of the formula. For example, at a Caloric density of 68 kcal/100 ml, the osmolality of the RTF (ready-to-feed) formula can range from 350–375 mOsm/kg $H_2O$. At a Caloric density of 135 kcal/100 ml, the osmolality of the formula can range from 850–900 mOsm/kg $H_2O$.

One aspect of the present invention resides in the use of corn syrup solids for the carbohydrate source. It is important to use a source of carbohydrate that will not adversely affect (increase to a high value) the osmolality of the final product particularly when L-amino acids supply the protein equivalent, since they are small molecules that add considerably to osmolality. Those skilled in the art will appreciate that high osmolalities (i.e., above about 450 mOsm/kg $H_2O$ for infants and about 750 mOsm/kg $H_2O$ for children) in a liquid nutrition product can cause gastric upset and diarrhea. Thus, the use of types of carbohydrates, such as dextrose and sucrose, which would increase the osmolality above about 400 mOsm/kg $H_2O$ for infants, and about 750 mOsm/kg $H_2O$ for children is discouraged. In a preferred embodiment, the carbohydrate used in the present invention has a DE (dextrose equivalent) of no more than 23 and is corn syrup solids. Use of a carbohydrate with a DE of greater than 23 in combination with L-amino acids will provide an osmotic pressure in the intestine that may lead to bloating, diarrhea and dehydration. These are conditions that should be avoided in patients already suffering from gastrointestinal problems. The medical food in accordance with this invention provides a good balance of Caloric density and acceptable osmolality. As those skilled in this art will appreciate, as the DE of the carbohydrate increases, the osmolality of the formula will also increase. The preferred source of carbohydrate is corn syrup solids with a DE of 23 or less.

Also contemplated in this invention is an elemental medical food that is flavored. Flavorings and sweeteners (preferably not sucrose or glucose) known in the food industry are acceptable provided the consuming patients are not allergic thereto and the osmolality of the final product is acceptable. A vanilla flavored product sweetened with the artificial sweetener aspartame (NutraSweet®) was produced based on Example 1. The osmolality of the flavored product at 68 kcal/100 ml was 370 mOsm/kg $H_2O$ and 895 mOsm/kg $H_2O$ at 135 kcal/100 ml.

There is also disclosed a lipid component for use in the present invention which comprises on a weight percent of the lipid component, 35 to 43% high oleic safflower oil, 28 to 35% fractionated coconut oil (MCT's), 24 to 30% soy oil, and 0.5 to 8% esterified glycerols. In the lipid component of this invention, the level of linoleic acid may range from 15 to 22% and the level of α-linolenic may range from 2 to 5% by weight of the total lipid component.

A representative blend of 6.4 gms of soy oil, 9.0 gms of high oleic safflower oil, 7.6 gms of fractionated coconut oil and 1.4 gms of DATEM were incorporated into the elemental medical food according to this invention and then analyzed for fatty acid content. Table I sets forth the name of the fatty acid, gms of fatty acid per 100 gms powder, % of energy and weight % of fat.

TABLE I

| NAME | NO. OF CARBONS | G/100 G[1] POWDER | % OF ENERGY | % OF FAT WT. |
|---|---|---|---|---|
| Caproic | C6:0 | 0.068 | 0.129 | 0.29 |
| Caprylic | C8:0 | 4.230 | 8.015 | 18.00 |
| Capric | C10:0 | 3.032 | 5.745 | 12.90 |
| Lauric | C12:0 | 0.042 | 0.080 | 0.18 |
| Palmitic | C16:0 | 1.191 | 2.257 | 5.07 |
| Palmitoleic | C16:1n7 | 0.014 | 0.027 | 0.06 |
| Stearic | C18:0 | 1.159 | 2.196 | 4.93 |
| Oleic | C18:1n9 | 8.342 | 15.806 | 35.50 |
| Linoleic | C18:2n6 | 4.653 | 8.816 | 19.80 |
| α-Linolenic | C18:3n3 | 0.531 | 1.006 | 2.26 |
| Arachidic | C20:0 | 0.067 | 0.127 | 0.29 |
| Eicosenoic | C20:1n9 | 0.046 | 0.087 | 0.19 |
| Behenic | C22:0 | 0.051 | 0.097 | 0.22 |
| Lignoceric | C24:0 | 0.024 | 0.045 | 0.10 |
| Nervonic | C24:1n9 | 0.018 | 0.034 | 0.08 |
| TOTALS | | 23.468 | 44.467 | 99.87 |
| Monounsaturated fatty acids | | 8.420 | 15.954 | 35.83 |
| Polyunsaturated fatty acids | | 5.184 | 9.822 | 22.06 |
| Saturated fatty acids | | 9.864 | 18.690 | 41.97 |

[1]Analytical data

On analysis, one cannot differentiate the fatty acids from Panodan, soy oil and HO safflower oil.

In a further embodiment of the present invention, there is disclosed a powdered, elemental medical food which comprises per 100 g of powder further described in Table II.

TABLE II

Elemental Medical Food

| | Range Per 100 g Product |
|---|---|
| Nitrogen, g | 2.32–2.92 |
| Protein Equivalent, g | 14.3–17.9 |
| Fat, g | 22.6–24.5 |
| Moisture, g | 1.0–2.0 |
| Ash, g | 3.0–4.5 |
| Carbohydrate, g | 46.7–56.0 |
| Calories | 475–495 |
| Vit. A, IU | 1500–2256 |
| Vit E., IU | 11.6–15.1 |
| Vit. D, IU | 260–317 |
| Vit. K, mcg | 70–103 |
| Pyridoxine, mg | 0.57–0.79 |
| Niacin, mg | 9.28–12.47 |
| Folic acid, mcg | 177–282 |
| Vit $B_1$, mg | 1.42–1.95 |
| Riboflavin, mg | 0.62–0.87 |
| Vit. $B_{12}$, mcg | 4.06–6.46 |
| Pantothenic acid, mg | 5.05–8.03 |
| Biotin, mcg | 50–82 |
| Vit. C, mg | 200–400 |
| Total Choline, mg | 36–65 |
| Inositol, mg | 32–42 |
| Calcium, mg | 515–600 |
| Phosphorous, mg | 385–465 |
| Ca/P | 1.11–1.56 |
| Magnesium, mg | 40.0–60.0 |
| Iron, mg | 8.4–11.4 |
| Zinc, mg | 5.40–7.1 |
| Manganese, mg | 0.50–0.70 |
| Copper, mg | 0.70–0.90 |
| Iodine, mcg | 28–56 |
| Selenium, mcg | 11.0–20.0 |
| Chromium, mcg | 11.0–20.0 |
| Molybdenum, mcg | 12.0–26.0 |
| Sodium, mg | 217–257 |
| Potassium, mg | 717–824 |
| Chloride, mg | 285–395 |
| Taurine, mg | 30–56 |
| L-Carnitine, mg | 23–31 |

Yet more specifically, the elemental food according to this invention comprises, based on 100 kcal of said composition, 2.8 to 3.8 g of protein equivalent, 4.0 to 5.6 g of fat, 9.0 to 11.8 g of carbohydrates, 0.4 to 0.8 g linoleic acid, 262 to 475 IU Vitamin A, 40 to 80 IU Vitamin D, 2.0 to 3.5 IU Vitamin E, 5 to 20 mcg Vitamin K, 0.11 to 0.42 mg thiamine, 0.1 to 0.21 mg riboflavin, 0.09 to 0.17 mg Vitamin B-6, 0.40 to 1.36 mcg Vitamin B-12, 1.6 to 3.2 mg niacin, 28 to 60 mcg folic acid, 0.40 to 1.70 mg pantothenic acid, 4.0 to 18 mcg biotin, 8.6 to 85 mg Vitamin C, 7.5 to 14.5 mg choline, 4.6 to 9.9 mg inositol, 4 to 6.5 mg L-carnitine, 103 to 127 mg calcium, 76 to 103 mg phosphorus, 8.0 to 12.7 mg magnesium, 1.6 to 2.4 mg iron, 1.0 to 1.7 mg zinc, 0.10 to 0.15 mg manganese, 0.11 to 0.19 mg copper, 6.7 to 11.8 mcg iodine, 2.2 to 4.7 mcg selenium, 2.2 to 4.7 mcg chromium, 2.4 to 5.5 mcg molybdenum, 40 to 55 mg sodium, 144 to 174 mg potassium and 55 to 85 mg chloride.

To convert values of nutrient per 100 kcal to values of nutrient per 100 gms of powdered product, one multiplies the 100 kcal value by 4.75.

The inclusion of nucleotides and/or nucleosides in the elemental food according to this invention is also contemplated. The teachings of U.S. Pat. No. 5,492,899 to Masor et al, U.S. Pat. No. 3,231,385 to Ziro et al., U.S. Pat. No. 4,544,559 to Gil and U.S. Pat. No. 4,994,442 to Gil et al., which relate to the inclusion of nucleotides in nutritional formulas, are incorporated herein by reference.

In another embodiment of the present invention, the protein equivalent component of the elemental medical food has an amino acid profile as set forth in Table III.

TABLE III

Amino Acid Profile of Protein Equivalent

| | MINIMUM gms/100 gms* | MAXIMUM gms/100 gms* | MINI-MUM** | MAXI-MUM** |
|---|---|---|---|---|
| L-alanine | 2.86 | 4.23 | 2.80 | 4.41 |
| L-arginine | 5.17 | 7.72 | 5.05 | 7.93 |
| L-asparagine | 8.37 | 12.42 | 8.35 | 13.10 |
| L-cystine | 1.10 | 1.68 | 1.10 | 1.72 |
| L-glutamine | 10.62 | 15.85 | 10.44 | 16.41 |
| Glycine | 2.20 | 3.29 | 2.20 | 3.45 |
| L-histidine | 2.20 | 3.29 | 2.14 | 3.38 |
| L-isoleucine | 5.72 | 8.53 | 5.60 | 8.83 |
| L-leucine | 9.25 | 13.83 | 9.12 | 14.28 |
| L-lysine | 5.17 | 7.66 | 5.05 | 7.93 |
| L-methionine | 2.15 | 3.22 | 2.09 | 3.31 |
| L-phenylalanine | 4.79 | 7.12 | 4.67 | 7.31 |
| L-proline | 2.92 | 4.16 | 2.80 | 4.41 |
| L-serine | 2.86 | 4.23 | 2.80 | 4.41 |
| L-threonine | 3.80 | 5.71 | 3.74 | 5.86 |
| L-tryptophan | 1.49 | 2.22 | 1.42 | 2.28 |
| L-tyrosine | 4.79 | 7.12 | 4.67 | 7.31 |
| L-valine | 6.55 | 9.74 | 6.43 | 10.07 |

*of amino acids
**as percent of protein equivalent

The Caloric density of the inventive formula is preferably from about 450 to 500 kcal/100 g of powder. The Caloric density of the RTF product can, of course, be adjusted through rate of dilution with water.

This invention relates to improved enteral nutritional hypoallergenic formulas and more particularly to hypoallergenic formulas which taste good. In addition, the nutrition product of this invention provides a nutritionally complete hypoallergenic food for individuals with multiple food allergies, short gut syndrome, cystic fibrosis, pancreatic disease, gastroenteritis, inflammatory bowel disease, intractable diarrhea, malnutrition, protein maldigestion, infectious diseases or for patients with hypermetabolism, such as burn and trauma victims or cancer patients.

The present invention also relates to a method for providing nutritional support to a human suffering from gastrointestinal conditions caused by food protein allergens or severe food allergies. The method comprises the enteral administration of the hypoallergenic medical food according to this invention to a human suffering from a protein allergen induced gastrointestinal condition.

The elemental food according to this invention is for enteral administration and is designed to provide complete nutrition (meets all RDA's) in a small volume. For example, when the RDA for energy for age is supplied by the instant elemental food, all nutrients meet both the USFDA Infant Formula Act specifications and RDA for age in volumes noted in

TABLE IV

| Age | Elemental Food, g | Add H20 to Make (mL) | Fl Oz | kcal/oz |
|---|---|---|---|---|
| 0 < 6 mo | 137 | 800 | 27 | 24 |
| 6 < 12 mo | 179 | 930 | 31 | 27 |
| 1 < 4 yr. | 274 | 1,272 | 43 | 30 |
| 4 < 7 yr. | 379 | 1,330 | 45 | 40 |
| 7 < 11 yr. | 421 | 1,478 | 50 | 40 |

The following Table V is a representative listing of ingredients and a range of % by weight for each component that can be used to prepare the palatable elemental medical food of this invention.

TABLE V

Bill of Materials

| Ingredient | Per 100 lbs. powder* |
|---|---|
| Pediatric Elemental Base | |
| Maltrin M200 | 53 lbs |
| Tricalcium phosphate | 1.30 lb |
| Dipotassium phosphate | 1.1927 lb |
| Sodium citrate | 0.7451 lb |
| Potassium citrate | 0.9258 lb |
| Magnesium chloride | 0.34 lb |
| Calcium carbonate | 0.1702 lb |
| Sodium chloride | 0.036 lb |
| Potassium Iodide | 0.000055 lb |
| High Oleic Safflower Oil | 8.9 lb |
| MCT oil | 7.5 lb |
| Soy oil | 6.4 lb |
| Panodan | 1.42 lb |
| Vitamin A, D3, E, K1 Concentrate | 0.0338 lb |
| Refined coconut oil | 7.86 g |
| Vitamin E acetate | 6.90 g |
| Vitamin A acetate | 540 mg |
| Phylloquinone (phytonadione) | 26.1 mg |
| Vitamin D3 | 3.83 mg |
| Ascorbyl Palmitate | 0.0282 lb |
| Beta Carotene | 0.0009 lb |

TABLE V-continued

Bill of Materials

| Ingredient | Per 100 lbs. powder* |
|---|---|
| Ascorbic Acid | 0.4343 lb |
| L-carnitine | 0.0269 lb |
| Vitamin/Mineral/Taurine premix | 0.2002 lb |
| Calcium phosphate, dibasic (premix diluent) | 25.4 g |
| Taurine | 25.0 g |
| m-Inositol | 18.4 g |
| Zinc sulfate | 7.59 g |
| Niacinamide | 5.25 g |
| Ferrous sulfate | 2.90 g |
| d-Calcium pantothenate | 2.84 g |
| Cupric sulfate | 1.57 g |
| Thiamine chloride hydrochloride | 804 mg |
| Riboflavin | 355 mg |
| Pyridoxine hydrochloride | 326 mg |
| Manganese sulfate | 187 mg |
| Folic acid | 99.9 mg |
| Biotin | 28.7 mg |
| Sodium selenite | 14.1 mg |
| Cyanocobalamin | 2.29 mg |
| Choline chloride | 0.0584 lb |
| Ferrous sulfate | 0.0324 lb |
| Potassium citrate | 0.0020 lb |
| Manganese sulfate | 0.0011 lb |
| Chromium chloride | 0.00005 lb |
| Sodium molybdate | 0.00004 lb |
| Amino Acid Premix: | 17.24 lb |
| L-Glutamine | 875.4 g |
| L-Asparagine monohydrate | 780.2 g |
| L-Leucine | 762.0 g |
| L-Lysine acetate | 598.7 g |
| L-Valine | 539.8 g |
| L-Isoleucine | 471.7 g |
| L-Arginine | 426.4 g |
| L-Phenylalanine | 394.6 g |
| L-Tyrosine | 394.6 g |
| L-Threonine | 313.0 g |
| L-Proline | 240.4 g |
| L-Alanine | 235.9 g |
| L-Serine | 235.9 g |
| Glycine | 181.4 g |
| L-Histidine | 181.4 g |
| L-Methionine | 176.9 g |
| L-Cystine dihydrochloride | 122.5 g |
| L-Tryptophan | 122.5 g |
| TOTAL | 99.99 lb* |

*values in kilograms are set forth in Table VII

A specific embodiment of an elemental formula in accordance with the present invention is set forth in Table VI.

TABLE VI

| NUTRIENT | PER 100 G POWDER | |
|---|---|---|
| Protein Equivalent, g | 14.3 | |
| Fat, g | 22.6 | |
| Carbohydrate, g | 46.7 | |
| Linoleic acid, g | 2.85 | |
| Linolenic acid, g | 0.48 | |
| Calories, kcal | 475 | |
| Calcium, mg | 515 | |
| Phosphorus, mg | 385 | |
| Magnesium, mg | 40 | |
| Sodium, mEq (mg) | 9.35 | (215) |
| Potassium, mEq (mg) | 18.29 | (715) |
| Chloride, mEq (mg) | 8.04 | (285) |
| Iron, mg | 8.4 | |
| Zinc, mg | 5.3 | |
| Copper, mg | 0.60 | |
| Iodine, mcg | 34 | |
| Manganese, mg | 0.50 | |
| Selenium, mcg | 11 | |

TABLE VI-continued

| NUTRIENT | PER 100 G POWDER | |
| --- | --- | --- |
| Vitamin A, mcg RE (IU) | 390 | (1300) |
| Vitamin D, mcg (IU) | 5 | (200) |
| Vitamin E, mg α-TE (IU) | 6.7 | (10.0) |
| Vitamin K, mcg | 30 | |
| Vitamin C, mg | 43 | |
| Thiamin, mg | 1.0 | |
| Riboflavin, mg | 0.5 | |
| Vitamin B-6, mg | 0.48 | |
| Vitamin $B_{12}$, mcg | 2.0 | |
| Niacin, mg | 8.0 | |
| Folic Acid, mcg | 140 | |
| Pantothenic Acid, mg | 2.0 | |
| Biotin, mcg | 20 | |
| Choline, mg | 38 | |
| Inositol, mg | 24 | |
| Chromium, mcg | 11 | |
| Molybdenum, mcg | 12 | |
| Taurine, mg | 30 | |
| L-carnitine, mg | 23 | |

The present invention will now be explained on the basis of some specific embodying examples, which, however, are to be considered as illustrative only. Unless otherwise noted, concentrations are parts by weight.

EXAMPLE 1

General Procedure

The teachings of U.S. Pat. No. 5,326,569 to Acosta et al. regarding the preparation of the amino acid mixtures and the process of preparing an elemental formula, are used in the preparation of the elemental formulas according to this invention and are thus incorporated herein by reference. An enteral formula in accordance with this invention is in general, accomplished through the dry blending of a powdered premix base with an amino acid premix. The production of the premixed base is accomplished through the steps summarized below:

1. Preparation of Stock Solutions
   a. Preparation of a water soluble vitamin and trace mineral mixture;
   b. Preparation of an ascorbic acid mixture;
   c. Preparation of oil blend containing oil soluble vitamins; and
   d. Preparation of a carbohydrate/mineral slurry.
2. Combination in a specified sequence of the Stock Solutions
   a. Mixing of the oil blend and carbohydrate/mineral slurry;
   b. Addition of the water soluble vitamins to the slurry; and
   c. Addition of ascorbic acid to the slurry.
3. Drying of the combined stock solutions to yield the powdered premix base
4. Dry blending of the powdered premix base, with an amino acid premix to yield the elemental formula according to the present invention

Commercial Scale

The clinical product utilized in Example 2 was produced on a commercial scale. A batch of 1,000 kg was produced using the method described above to insure label composition over shelf life as set forth in Table VII.

TABLE VII

| INGREDIENTS | AMOUNT (kg) |
| --- | --- |
| MCT Oil | 75.000 |
| Soy Oil | 64.000 |
| HO Safflower Oil | 89.000 |
| Oil Soluble Vit. Premix | 0.338 |
| Panodan | 14.200 |
| Sodium Citrate | 7.451 |
| Sodium Chloride | 0.360 |
| Potassium Citrate | 9.258 |
| Potassium Iodide | 0.0005 |
| Magnesium Chloride | 0.340 |
| Potassium Phosphate Dibasic | 7.451 |
| Calcium Carbonate | 1.702 |
| umTCP (Ultramicronized Tricalcium Phosphate) | 1.300 |
| Maltrin M200 | 530. |
| Ferrous Sulfate | 0.324 |
| Premix 1870 | 2.002 |
| Manganese Sulfate | 0.011 |
| Choline Chloride | 0.584 |
| L-Carnitine | 0.269 |
| Chromium Chloride | 0.005 |
| Sodium Molybdate | 0.003 |
| Ascorbic Acid | 4.343 |
| Beta Carotene | 0.009 |
| Ascorbyl Palmitate | 0.282 |
| L-Alanine | 5.70 |
| L-Asparagine Monohydrate | 19.15 |
| Glycine | 4.45 |
| L-Arginine | 10.40 |
| L-Cystine 2-HCl | 3.00 |
| L-Glutamine | 21.45 |
| L-Histidine | 4.45 |
| L-Isoleucine | 11.55 |
| L-Lysine Acetate | 14.65 |
| L-Leucine | 18.70 |
| Phenylalanine | 9.65 |
| L-Threonine | 7.70 |
| L-Tryptophan | 3.00 |
| L-Tyrosine | 9.65 |
| L-Valine | 13.20 |
| L-Methionine | 4.30 |
| Proline | 5.70 |
| Serine | 5.70 |
| TOTAL | 1000.06 |

EXAMPLE 2

A clinical study of the inventive formula was conducted at The Johns Hopkins Hospital (Baltimore, Md.) to assess the growth, tolerance and biochemical response of children fed the formula according to the present invention as a primary feeding for four (4) months. The children, while consuming the inventive formula, were on diets free from known food allergens to which they were sensitive. The primary indicators used to evaluate the formula according to the invention were weight, height, intake, stool patterns, blood biochemistry (complete blood count, serum albumin, ferritin, transthyretin, retinol binding protein, retinol and urea nitrogen, and plasma amino acids), and stool occult blood assessment. Secondary variables included gastrointestinal symptoms.

The non-randomized feeding study was conducted with fourteen (14) children with protein sensitive eosinophilic gastroenteritis or multiple food protein sensitivity. Each child served as his/her own control. All subjects prior to admission to the study were subjected to a double blind, placebo-controlled food challenges with the child's current formula and the inventive composition to determine if it elicited any allergic symptoms. Previous medical records, growth history for up to the past twelve (12) months, detailed medical and dietary histories and records of oral challenge results for each subject were obtained.

The elemental product produced in Example 1 was provided as a powder in 350 g cans and was reconstituted to meet the individualized needs of each child as determined by the research dietitian. The inventive formula was flavored with approved flavorings determined by the investigator. Children were allowed to ingest only those foods that could be tolerated, the study formula and flavorings approved by the investigator.

On Day 1 of the study, blood and stool samples were collected and subjects were again assessed at one (1) and four (4) month post-start dates for growth, formula intake, tolerance and blood and stool parameters (4 months only).

Subjects were removed from the study on the basis of a protocol failure or a treatment failure. A child was considered a protocol failure if he or she failed to comply with scheduled examination, was voluntarily removed by the parent, failed to consume sufficient amounts of the study formula or removed by the physician because he or she believed it was in the child's best interest. Children were considered a treatment failure if they were unable to consume the study formula due to intolerance or an allergic reaction to the study formula.

Careful measurements of weight, height and head circumference were made upon enrollment into the study, at each visit and at study exit using standard techniques and equipment. Available weight and height data collected during the one-year period prior to the start of the study were used for historical comparisons.

At the four-month point, the elemental product produced in Example 1 was supplying an average of 58% of total calories per day for the children, with the remainder being supplied by authorized (i.e., tolerized foods) foods. In general, the children maintained growth while on the study formula. Only one subject experienced a slight decrease in rate of growth while consuming the study formula and this may have been caused by problems at home (parental separation).

The children in the study often had little appetite for solid foods and weight gains would have improved if energy intakes were increased to meet the recommended RDA. Hemoglobin and hematocrit concentrations in study subjects were significantly improved during the study period. Other blood chemistries assessed were generally maintained at levels similar to those at entrance. Insufficient data were available at the time of filing this application to assess the effect of the study formula on serum vitamins. Data is continuing to be collected in this study and will be statistically analyzed.

Stool patterns improved slightly during the study period; in fact, two children were able to be toilet trained after going on the study formula due to improvement in their stools compared to their previous feeding.

In conclusion, the preliminary results of the study support the formula according to the invention is a hypoallergenic formula suitable for use in the management of children with multiple food allergies or allergic eosinophilic gastroenteritis. Children grew acceptably on the inventive product when it provided the majority of the energy needs. The children tolerated the study product well and found its taste acceptable. Anecdotal comments from parents and site personnel have been positive. Data continue to be collected and statistical analysis will be conducted at the conclusion of data collection.

EXAMPLE 3

The hypoallergenic formula in accordance with this invention was analyzed for protein efficiency ratio (PER), which is a measure of protein quality using laboratory rats. PER is determined by dividing the animals weight gain by protein intake. Two groups of ten rats each, were fed a diet for 28 days of the hypoallergenic formula and a casein based formula using AOAC method-960.48, AOAC *Official Methods of Analysis,* 15th Edition, 1990. Every seven days, the rats were weighed and their food consumption was recorded. At the end of 28 days, the total weight gain and protein composition of the two groups were calculated. These values were used to calculate the PER.

The results of this rat bioassay, set forth in Table VIII, indicate that the pediatric elemental diet, in accordance with the present invention has a significantly greater protein efficiency ratio than the conventional casein based formula.

TABLE VIII

| CASEIN COMPOSITION Body Weights - Grams | | | | | | | PEDIATRIC ELEMENTAL Body Weights - Grams | | | | | | |
|---|---|---|---|---|---|---|---|---|---|---|---|---|---|
| Animal No. | Week 0 | Week 1 | Week 2 | Week 3 | Week 4 | Wt. Gain | Animal No. | Week 0 | Week 1 | Week 2 | Week 3 | Week 4 | Wt. Gain |
| 1 | 76 | 86 | 124 | 158 | 199 | 123 | 1 | 71 | 96 | 133 | 184 | 237 | 166 |
| 2 | 71 | 88 | 130 | 170 | 199 | 128 | 2 | 70 | 93 | 133 | 179 | 245 | 175 |
| 3 | 72 | 90 | 122 | 150 | 190 | 118 | 3 | 81 | 99 | 137 | 187 | 237 | 156 |
| 4 | 72 | 86 | 133 | 159 | 201 | 129 | 4 | 75 | 97 | 145 | 207 | 266 | 191 |
| 5 | 82 | 94 | 123 | 153 | 191 | 109 | 5 | 76 | 97 | 133 | 174 | 212 | 136 |
| 6 | 79 | 107 | 150 | 192 | 232 | 153 | 6 | 67 | 95 | 133 | 187 | 236 | 169 |
| 7 | 75 | 91 | 125 | 159 | 212 | 137 | 7 | 84 | 111 | 167 | 232 | 293 | 209 |
| 8 | 78 | 89 | 127 | 158 | 195 | 117 | 8 | 80 | 103 | 144 | 200 | 247 | 167 |
| 9 | 68 | 85 | 119 | 149 | 197 | 129 | 9 | 73 | 100 | 146 | 190 | 233 | 160 |
| 10 | 74 | 96 | 129 | 163 | 197 | 123 | 10 | 74 | 96 | 145 | 183 | 231 | 157 |
| Mean | 75 | 91 | 128 | 161 | 201 | 127 | Mean | 75 | 99 | 141 | 192 | 244 | 169 |
| SD | 4.19 | 6.52 | 8.73 | 12.57 | 12.27 | 12.05 | SD | 5.3 | 5.08 | 10.72 | 17.19 | 22.11 | 20.14 |

| CASEIN COMPOSITION Feed Consumption - Grams | | | | | | | PEDIATRIC ELEMENTAL Feed Consumption - Grams | | | | | | |
|---|---|---|---|---|---|---|---|---|---|---|---|---|---|
| Animal No. | Wk 1 | Wk 2 | Wk 3 | Wk 4 | Total | Protein | PER | Animal No. | Wk 1 | Wk 2 | Wk 3 | Wk 4 | Total | Protein | PER |
| 1 | 62 | 102 | 116 | 133 | 412 | 42 | 2.92 | 1 | 81 | 101 | 134 | 144 | 460 | 45 | 3.69 |
| 2 | 78 | 120 | 149 | 133 | 479 | 48.9 | 2.62 | 2 | 80 | 105 | 129 | 157 | 472 | 46.3 | 3.78 |

TABLE VIII-continued

| | | | | | | | | | | | | | | | |
|---|---|---|---|---|---|---|---|---|---|---|---|---|---|---|---|
| 3 | 71 | 94 | 110 | 123 | 399 | 40.7 | 2.89 | 3 | 79 | 109 | 139 | 166 | 492 | 48.2 | 3.23 |
| 4 | 62 | 113 | 114 | 139 | 428 | 43.7 | 2.96 | 4 | 79 | 115 | 150 | 158 | 502 | 49.2 | 3.89 |
| 5 | 73 | 95 | 104 | 128 | 399 | 40.7 | 2.67 | 5 | 77 | 97 | 122 | 144 | 439 | 43.1 | 3.16 |
| 6 | 90 | 118 | 133 | 138 | 479 | 48.8 | 3.12 | 6 | 80 | 106 | 137 | 143 | 466 | 45.6 | 3.70 |
| 7 | 75 | 104 | 121 | 138 | 438 | 44.7 | 3.06 | 7 | 90 | 136 | 163 | 162 | 551 | 54 | 3.87 |
| 8 | 62 | 110 | 115 | 133 | 421 | 42.9 | 2.73 | 8 | 86 | 110 | 146 | 147 | 489 | 48 | 3.48 |
| 9 | 67 | 90 | 109 | 130 | 396 | 40.4 | 3.2 | 9 | 90 | 121 | 131 | 129 | 471 | 46.1 | 3.46 |
| 10 | 85 | 98 | 124 | 125 | 432 | 44.1 | 2.79 | 10 | 80 | 113 | 124 | 134 | 450 | 44.1 | 3.56 |
| Mean | 73 | 104 | 119 | 132 | 428 | 43.7 | 2.9 | Mean | 82.1 | 111 | 137 | 148 | 479 | 46.9 | 3.58 |
| SD | 9.74 | 10.39 | 13.23 | 5.52 | 30.4 | 3.1 | 0.195 | SD | 4.67 | 11.1 | 12.6 | 12.23 | 31.74 | 3.11 | 0.253 |

EXAMPLE 4

Immunogenicity

This experiment was conducted to evaluate the allergenic potential of the elemental medical food of this invention (produced in Example 1) compared to three commercially available hypoallergenic nutritionals. Low immunogenicity demonstrated in this experiment is highly predictive of very low allergenic activity of a nutritional product.

The three commercially available products were Neocate®, Neocate® One+ and Vivonex® Pediatric. In this experiment, rabbits were hyperimmunized with the nutritional according to this invention or the aforementioned commercial products using a vigorous immunization protocol employing Complete Freunds' Adjuvant (CFA) with multiple injections. Enzyme-linked immunosorbent assay (ELISA) was used to measure the systemic (IgG) antigen-specific immune response of the rabbits and to define the relative immunogenicity of each product. A more detailed understanding of immunogenicity evaluation of proteins can be obtained from a review of the following articles:

1) Cordle et al., "Immunogenicity Evaluation of Protein Hydrolysates for Hypoallergenic Infant Formula", J. of Ped. Gastro. and Nut., 13:270–276 (1991)

2) Cordle, "Control of Food Allergies Using Protein Hydrolysates", Food Technology, October 1994; and 3) Cordle et al., "Evaluation of the immunogenicity of protein hydrolysate formulas using laboratory animal hyperimmunization", Pediatr. Allergy Immunol, 5:14–19, (1994).

The teachings of the three listed articles are incorporated herein by reference.

Samples of each product w ere mixed with sterile phosphate buffered saline (PBS) to result in a concentration of 5 mg protein (amino acids) per 1.5 ml (PBS solution). The primary immunization was prepared by emulsifying 1.5 ml of the PBS product solution with 3.0 ml of CFA. The booster immunization was prepared by mixing 1.5 ml of each PBS solution with 1.5 ml of CFA. These samples were then administered at a dose of 5 mg protein equivalent per each of two immunizations.

The animals were placed on a vegetable diet (milk, soy and rice free) for 14 days prior to the primary immunization and remained on this diet for the duration of the study. Pre-immunization blood samples were taken from each rabbit on day 0, and then each rabbit was immunized. On day 21, a second immunization was conducted. The animals were exsanguinated on day 35. Serum was collected and stored at −20° C. until testing.

Antibody responses were quantitated by an ELISA developed for each antigen as follows. ELISA plates were coated with the immunizing formula at an optimal (saturating) concentration. The plates were blocked with PBS containing 0.05% egg albumin and 0.1% Tween 20 to eliminate non-specific binding. Test antisera were serially diluted and added to the coated plates. Next goat anti-rabbit IgG horseradish peroxidase conjugate was added to react with any rabbit antibody bound to the immunogen. Addition of the enzyme substrate (tetramethylbenzidine) caused a color change that was directly proportional to the amount of antibody bound. Antibody titer was defined as the reciprocal of the dilution of serum which gave an ELISA optical density of 0.3 at 450 nm 10 minutes after the enzyme substrate addition.

Five (5) rabbits were immunized with each nutritional product. The data contained in Table IX sets forth the mean titer for each group of five rabbits and the standard deviations on day 0 and day 35.

TABLE IX

| FORMULA | DAY | MEAN TITER | SD |
|---|---|---|---|
| Ex. 1 | 0 | 21 | 12 |
| | 35 | 119* | 83 |
| Neocate | 0 | 92 | 24 |
| | 35 | 389* | 222 |
| Neocate One + | 0 | 351 | 111 |
| | 35 | 56,000 | 27,505 |
| Vivonex Pediatric | 0 | 304 | 185 |
| | 35 | 646* | 469 |

SD = standard deviation
*= not significantly different

While the titers for the formula according to this invention were actually lower than all of the commercial products, it can only be concluded that the elemental formula produced in Ex. 1 was far superior to Neocate One+. It can also be concluded that the formula according to the invention demonstrates very low immunogenicity, indicating that the product according to the invention will demonstrate clinical hypoallergenic performance. Further, these data support the use of the instant invention for people that are exquisitely sensitive to milk proteins or that react to extensively hydrolyzed protein formulas.

EXAMPLE 5

Organoleptic Test

One important aspect of this invention resides in the taste of the formula made in accordance with the invention. Most elemental medical foods presently available have a highly unpleasant taste and, as such, patients using these formulas are less likely to consume the necessary Caloric intake or may even be non-compliant with therapy.

The elemental medical food produced in Example 1 was taste tested against four commercially available formulas.

The product name and sample number for each product evaluated is set forth in Table X.

TABLE X

| SAMPLE | COMMERCIAL NAME | SUPPLIER |
|---|---|---|
| Ex. 1 | Present Invention | Abbott Laboratories |
| A | Vivonex Pediatric | Sandoz Nutrition Company |
| B | Neocate | SHS |
| C | Neocate One + | SHS |
| D | Elemental 028 | SHS |

All samples were supplied as unflavored powders and were reconstituted with water as shown in Table XI.

TABLE XI

| SAMPLE | WT. OF POWDER | WT. OF WATER |
|---|---|---|
| Ex. 1 | 354 g | 1301 g |
| A | 194 g | 594 g |
| B | 342 g | 1420 g |
| C | 100 g | 340 g |
| D | 200 g | 674 g |

Fifty-one (51) volunteers were recruited to evaluate the relative acceptability of a formula according to this invention compared to the 4 commercially available elemental medical foods. The procedure for this organoleptic evaluation consisted of providing a sample of the inventive formula to each evaluator, having them taste it and then comparing the taste of the 4 commercial formulas to the taste of the inventive formula. Each sample was evaluated at 24° C. and evaluated with the following scale:

| | |
|---|---|
| 9 = Extremely better than Ex. 1 | 4 = Slightly worse than Ex. 1 |
| 8 = Very much better than Ex. 1 | 3 = Moderately worse than Ex. 1 |
| 7 = Moderately better than Ex. 1 | 2 = Very much worse than Ex. 1 |
| 6 = Slightly better than Ex. 1 | 1 = Extremely worse than Ex. 1 |
| 5 = Neither better nor worse than Ex. 1 | |

The raw data from each evaluator was collected. Means, standard deviations and p-values were calculated. Significance was determined at the 95% Confidence Level, Turkey Criteria. Comparison of Ex. 1 was considered significant if the p-value was <0.0125, using Bonferroni Criteria. The results of this organoleptic test are set forth in Table XII.

TABLE XII

| SAMPLE | MEAN | STATISTICAL GROUP | P < or > 5 |
|---|---|---|---|
| A | 2.63 | C | 0.0000 |
| B | 4.16 | B | 0.0000 |
| C | 5.08 | A | 0.6623 |
| D | 5.06 | A | 0.7433 |

Samples which share a letter under the heading Statistical Group are not significantly different. From the data presented in Table IX, it is evident that commercial products A and B were significantly worse than Ex. 1. Thus, the formula according to this invention provides an elemental medical food that possesses highly acceptable flavor.

Industrial Applicability

This invention provides a palatable, hypoallergenic/ elemental product for the nutritional maintenance of humans that suffer from protein allergies. The medical community is constantly in search of improved formulations for their patients that supply a complete diet in a pleasant tasting matrix. As demonstrated in the examples, the formula in accordance with the present invention is easily manufactured and provides acceptable growth and tolerance to patients consuming same.

The embodiments of the present invention may, of course, be carried out in other specific ways than those set forth herein without departing from the spirit and essential characteristics of the invention. The present embodiments are therefore, to be considered in all respects as illustrated and not restrictive.

We claim:

1. A nutritionally complete elemental medical food suitable for use as the sole source of nutrition for a human comprising:

a) a carbohydrate component which comprises from 38 to 56% of the total Caloric content of said food;

b) a lipid component which comprises from 38 to 50% of the total Caloric content of said food and in which said lipid component comprises, based upon the weight of the lipid component, 35 to 43% high-oleic safflower oil, 28 to 35% fractionated coconut oil, 0.5 to 8% esterified glycerols, and 24 to 30% soy oil;

c) a blend of free L-amino acids which comprises from 10 to 20% of the total Caloric content of said food and wherein said amino acid blend comprises, the following essential amino acids; L-histidine, L-isoleucine, L-leucine, L-lysine, L-methionine, L-phenylalanine, L-threonine, L-tryptophan, and L-valine;

d) meets the recommended dietary allowances for a 1 to 3 year old child in a minimum of 1000 kilo calories;

e) based upon the weight of the elemental food comprises less than 50 ppm of L-glutamic acid and less than 50 ppm of L-aspartic acid, and;

f) based upon the weight of the amino acid blend comprises at least 8.37 wt. % L-asparagine and at least 10.6 wt % L-glutamine.

2. The elemental medical food according to claim 1 wherein said amino acid component comprises, based upon the weight of the amino acid component: 2.3 to 3.2 wt % -L-histidine; 5.9 to 8.5 wt %-L-isoleucine; 9.5 to 14.0 wt %-L-leucine; 6.6 to 9.7 wt %-L-valine; 5.2 to 7.6 wt %-L-lysine; 2.2 to 3.2 wt %-L-methionine; 4.9 to 7.1 wt %-L-phenylalanine; 3.8 to 5.7 wt %-L-threonine; 1.4 to 2.2 wt %-L-tryptophan; 3.0 to 4.2 wt %-L-alanine; 5.3 to 7.7 wt %-L-arginine; 8.6 to 12.4% L-asparagine monohydrate; 1.1 to 1.9%-L-cystine dihydrochloride; 11.0 to 15.8 wt %-L-glutamine; 2.3 to 3.2 wt %-glycine; 3.0 to 4.1 wt % L-proline; 3.0 to 4.2 wt %-L-serine; and 5.0 to 7.1 wt %-L-tyrosine.

3. The elemental food according to claim 1 in which said essential amino acids are present in the following amounts, based on the weight of the amino acid blend, at least 2.2 wt. % L-histidine, at least 5.72 wt. % L-isoleucine, at least 9.25 wt. % L-leucine, at least 5.17 wt. % L-lysine, at least 2.15 wt. % L-methionine, at least 4.79 wt. % L-phenylalanine, at least 3.8 wt. % threonine, at least 1.49 wt. % tryptophan, and at least 6.55 wt. % L-valine.

4. The elemental medical food according to claim 1 wherein said carbohydrate component consists essentially of corn syrup solids with a DE of 23 or less.

5. The elemental food according to claim 1 in which said lipid component comprises from 38 to 46% of the total caloric content of said food.

6. The elemental medical food according to claim 1 which is in powder form.

7. The elemental medical food according to claim 1 wherein about 4 grams of said composition is added to water to make about 30 ml and has an osmolality of 300 to 400 mOsm/kg $H_2O$.

8. The elemental medical food according to claim 1 which additionally comprises at least one element selected from the group consisting of nucleosides, nucleotides, antioxidant system, natural flavor, artificial flavors, artificial sweeteners, major trace and ultratrace minerals, minerals, vitamins and m-inositol.

9. The elemental medical food according to claim 7 wherein said composition has a Caloric density of about 0.68 kcalories/ml and an osmolality of 350 to 375 mOsm/kg $H_2O$.

10. The elemental medical food according to claim 1 which comprises, based on 100 kcalories of said composition: 2.8 to 3.8 g protein equivalent; 4.0 to 5.6 g fat, 9.0 to 11.8 g carbohydrate; 0.4 to 0.8 g linoleic acid; 262 to 475 IU Vitamin A; 40 to 80 IU Vitamin D; 2.0 to 3.5 IU Vitamin E; 5 to 20 mcg Vitamin K; 0.11 to 0.42 mg thiamine, 0.1 to 0.21 mg riboflavin; 0.09 to 0.17 mg Vitamin B-6; 0.40 to 1.36 mcg Vitamin B-12; 1.6 to 3.2 mg niacin; 28 to 60 mcg folic acid; 0.40 to 1.70 mg pantothenic acid; 4.0 to 18.0 mcg biotin; 8.6 to 85 mg Vitamin C; 7.5 to 14.6 mg choline; 4.6 to 9.9 mg inositol; 4.0 to 6.5 mg L-carnitine; 103 to 127 mg calcium; 76 to 103 mg phosphorus; 8.0 to 12.7 mg magnesium; 1.6 to 2.4 mg iron; 1.0 to 1.7 mg zinc; 0.10 to 0.15 mg manganese; 0.11 to 0.19 mg copper; 6.7 to 11.8 mcg iodine; 2.2 to 4.7 mcg selenium; 2.2 to 4.7 mcg chromium; 2.4 to 5.5 mcg molybdenum; 40 to 55 mg sodium; 144 to 174 mg potassium and 55 to 85 mg chloride.

11. The elemental medical food according to claim 6 which comprises, based on 100 grams of powder: 14.3 g protein equivalent; 22.6 g lipid; 46.7 g carbohydrate; 2.85 g linoleic acid; 0.48 g α-linolenic acid; 515 mg calcium; 385 mg phosphorous; 390 mcg Vitamin A; 5 mcg Vitamin D; 6.7 mg Vitamin E; 30 mcg Vitamin K; 1.0 mg thiamine, 0.50 mg riboflavin; 0.48 mg Vitamin B-6; 2.0 mcg Vitamin B-12; 8.0 mg niacin; 140 mcg folic acid; 2.0 mg pantothenic acid; 20 mcg biotin; 43 mg Vitamin C; 38 mg choline; 24 mg inositol; 23 mg L-caritine; 40 mg magnesium; 8.4 mg iron; 5.3 mg zinc; 0.50 mg manganese; 0.60 mg copper; 34 mcg iodine; 11 mcg selenium; 11 mcg chromium; 12 mcg molybdenum; 9.35 mEq sodium; 18.29 mEq potassium and 8.04 mEq chloride.

12. A method for providing nutritional support to a human suffering from food protein allergens, said method comprises the enteral administration of a nutritionally complete elemental medical food suitable for use as the sole source of nutrition comprising:

a) a carbohydrate component which comprises from 38 to 56% of the total Caloric content of said food;

b) a lipid component which comprises from 38 to 50% of the total Caloric content of said food and in which said lipid component comprises, based upon the weight of the lipid component, 35 to 43% high-oleic safflower oil, 28 to 35% fractionated coconut oil, 0.5 to 8% esterified glycerols, and 24 to 30% soy oil;

c) a blend of free L-amino acids which comprises from 10 to 20% of the total Caloric content of said food and wherein said amino acid blend comprises, the following essential amino acids, L-histidine, L-isoleucine, L-leucine, L-lysine, L-methionine, L-phenylalanine, L-threonine, L-tryptophan, and L-valine;

d) meets the recommended dietary allowances for a 1 to 3 year old child in a minimum of 1000 kilo calories;

e) based upon the weight of the elemental food comprises less than 50 ppm of L-glutamic acid and less than 50 ppm of L-aspartic acid, and;

f) based upon the weight of the amino acid blend comprises at least 8.37 wt. % L-asparagine and at least 10.6 wt % L-glutamine.

13. The method according to claim 12 wherein the gastrointestinal condition is selected from the group consisting of eosinophilic gastroenteritis, short gut syndrome, gastroenteritis, inflammatory bowel disease, intractable diarrhea and gastroesophogeal reflux.

14. The method according to claim 12 wherein the elemental medical food comprises, based on 100 kcal of said composition: 2.8 to 3.8 g protein equivalent; 4.0 to 5.6 g fat, 9.0 to 11.8 g carbohydrate; 0.4 to 0.8 g linoleic acid; 262 to 475 IU Vitamin A; 40 to 80 IU Vitamin D; 2.0 to 3.5 IU Vitamin E; 5 to 20 mcg Vitamin K; 0.11 to 0.42 mg thiamine, 0.1to 0.21 mg riboflavin; 0.09 to 0.17 mg Vitamin B-6; 0.40 to 1.36 mcg Vitamin B-12; 1.6 to 3.2 mg niacin; 28 to 60 mcg folic acid; 0.40 to 1.70 mg pantothenic acid; 4.0 to 18.0 mcg biotin; 8.6 to 85 mg Vitamin C; 7.5 to 14.6 mg choline; 4.6 to 9.9 mg inositol; 4.0 to 6.5 mg L-carnitine; 103 to 127 mg calcium; 76 to 103 mg phosphorus; 8.0 to 12.7 mg magnesium; 1.6 to 2.4 mg iron; 1.0 to 1.7 mg zinc; 0.10 to 0.15 mg manganese; 0.11 to 0.19 mg copper; 6.7 to 11.8 mcg iodine; 2.2 to 4.7 mcg selenium; 2.2 to 4.7 mcg chromium; 2.4 to 5.5 mcg molybdenum; 40 to 55 mg sodium; 144 to 174 mg potassium and 55 to 85 mg chloride.

15. A method for the nutrition support of a human suffering from a malady selected from the group consisting of severe food allergies, short gut syndrome, cystic fibrosis, pancreatic disease, gastroenteritis, inflammatory bowel disease, intractable diarrhea, malnutrition, protein maldigestion, necrotizing enterocolitis, infectious diseases, hypermetabolism, trauma, cancer, AIDS, eosinophilic gastroenteritis and gastroesophogeal reflux; said method comprising the administration to said human of a medical food suitable for use as the sole source of nutrition comprising:

a) a carbohydrate component which comprises from 38 to 56% of the total Caloric content of said food;

b) a lipid component which comprises from 38 to 50% of the total Caloric content of said food and in which said lipid component comprises, based upon the weight of the lipid component, 35 to 43% high-oleic safflower oil, 28 to 35% fractionated coconut oil, 0.5 to 8% esterified glycerols, and 24 to 30% soy oil;

c) a blend of free L-amino acids which comprises from 10 to 20% of the total Caloric content of said food and wherein said amino acid blend comprises the following essential amino acids; L-histidine, L-isoleucine, L-leucine, L-lysine, L-methionine, L-phenylalanine, L-threonine, L-tryptophan, and L-valine;

d) meets the recommended dietary allowances for a 1 to 3 year old child in 1000 kilo calories;

e) based upon the weight of the elemental food comprises less than 50 ppm of L-glutamic acid and less than 50 ppm of L-aspartic acid, and;

based upon the weight of the amino acid blend comprises at least 8.37 wt. % L-asparagine and at least 10.6 wt % L-glutamine.

* * * * *